(12) United States Patent
Bucchi Alencastre Moroz et al.

(10) Patent No.: US 9,918,913 B2
(45) Date of Patent: Mar. 20, 2018

(54) NANOSTRUCTURED CONDITIONING COSMETIC COMPOSITION, THE USE THEREOF IN COSMETIC PREPARATIONS, AND A CONDITIONING SHAMPOO

(71) Applicant: Natura Cosméticos S.A., São Paulo (BR)

(72) Inventors: Juliana Bucchi Alencastre Moroz, São Paulo (BR); Fabiano Leme Da Silva, Jundiaí (BR); Daniela Santos Ferreira Adami, São Paulo (BR); Paula Marina Souza De Oliveira, Campinas (BR); Candice Caroline Felippi, Porto Alegre (BR); Renata Platcheck Raffin, Porto Alegre (BR); Federico Alfredo Kladt Kladt, Franco da Rocha (BR)

(73) Assignee: NATURA COSMÉTICOS S.A., São Paulo-SP (BR)

(*) Notice: Subject to any disclaimer, the term of this patent is extended or adjusted under 35 U.S.C. 154(b) by 0 days.

(21) Appl. No.: 15/033,357

(22) PCT Filed: Oct. 30, 2014

(86) PCT No.: PCT/BR2014/050005
§ 371 (c)(1),
(2) Date: Apr. 29, 2016

(87) PCT Pub. No.: WO2015/061878
PCT Pub. Date: May 7, 2015

(65) Prior Publication Data
US 2016/0271024 A1    Sep. 22, 2016

Related U.S. Application Data

(60) Provisional application No. 61/897,492, filed on Oct. 30, 2013.

(51) Int. Cl.
*A61Q 5/02* (2006.01)
*A61K 8/11* (2006.01)
(Continued)

(52) U.S. Cl.
CPC ............... *A61K 8/11* (2013.01); *A61K 8/416* (2013.01); *A61K 8/4973* (2013.01); *A61K 8/602* (2013.01);
(Continued)

(58) Field of Classification Search
CPC ....... A61K 2800/413; A61Q 5/02; A61Q 5/12
See application file for complete search history.

(56) References Cited

U.S. PATENT DOCUMENTS

2003/0190302 A1   10/2003   Frantz et al.
2006/0024248 A1    2/2006   Spengler et al.
(Continued)

FOREIGN PATENT DOCUMENTS

EP    1 430 867 A1 *   6/2004
EP    1430867           6/2004
(Continued)

OTHER PUBLICATIONS

Pardeike J et al: "Lipid nanoparticles (SLN, NLC) in cosmetic and pharmaceutical dermal products", International Journal of Pharmaceutics, Elsevier BV, NL, vol. 366, No. 1-2, Jan. 21, 2009 (Jan. 21, 2009), pp. 170-184, XP025839914, ISSN: 0378-5173, DOI: 10.1016/J.IJPHARM.2008.10.003.
(Continued)

*Primary Examiner* — Carlos A Azpuru
(74) *Attorney, Agent, or Firm* — B. Aaron Schulman, Esq.; Stites & Harbison, PLLC.

(57) ABSTRACT

The present invention relates to conditioning cosmetic compositions comprising a nanostructured system formed by lipidic nanoparticles based on at least one from oil, butter
(Continued)

and wax, which encapsulate at least one cationic surfactant, as well as the use thereof in cosmetic preparations. Besides, the invention relates to a conditioning shampoo comprising said cosmetic composition.

21 Claims, 5 Drawing Sheets

(51) Int. Cl.
| | |
|---|---|
| *A61K 8/41* | (2006.01) |
| *A61Q 5/12* | (2006.01) |
| *A61K 8/92* | (2006.01) |
| *A61K 8/49* | (2006.01) |
| *A61K 8/60* | (2006.01) |
| *A61K 8/891* | (2006.01) |
| *A61K 8/892* | (2006.01) |

(52) U.S. Cl.
CPC .............. *A61K 8/891* (2013.01); *A61K 8/892* (2013.01); *A61K 8/922* (2013.01); *A61Q 5/02* (2013.01); *A61Q 5/12* (2013.01); *A61K 2800/412* (2013.01); *A61K 2800/56* (2013.01); *A61K 2800/652* (2013.01)

(56) References Cited

U.S. PATENT DOCUMENTS

| | | |
|---|---|---|
| 2012/0171263 A1 | 7/2012 | Capelas Romeu et al. |
| 2012/0213722 A1 | 8/2012 | Frantz et al. |
| 2013/0171088 A1 | 7/2013 | Frantz et al. |
| 2014/0065088 A1 | 3/2014 | Frantz et al. |

FOREIGN PATENT DOCUMENTS

| | | |
|---|---|---|
| FR | 2920983 | 3/2009 |
| WO | WO-2011/116963 | 9/2011 |

OTHER PUBLICATIONS

International Search Report for PCT/BR2014/050005 dated Feb. 3, 2015.
Written Opinion of the International Preliminary Examining Authority for PCT/BR2014/050005 dated Jan. 12, 2016.
Written Opinion of the International Searching Authority for PCT/BR2014/050005 dated Feb. 3, 2015.
International Preliminary Report on Patentability for PCT/BR2014/050005 completed Mar. 11, 2016.

* cited by examiner

Hair substantivity study. The letters indicate the statistic diferences (ANOVA 95%).

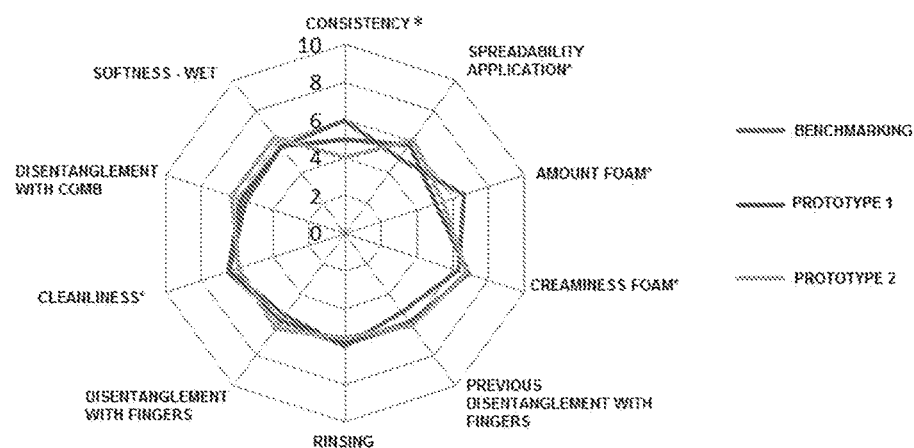
Fig. 5A – Evaluation of the wet hair
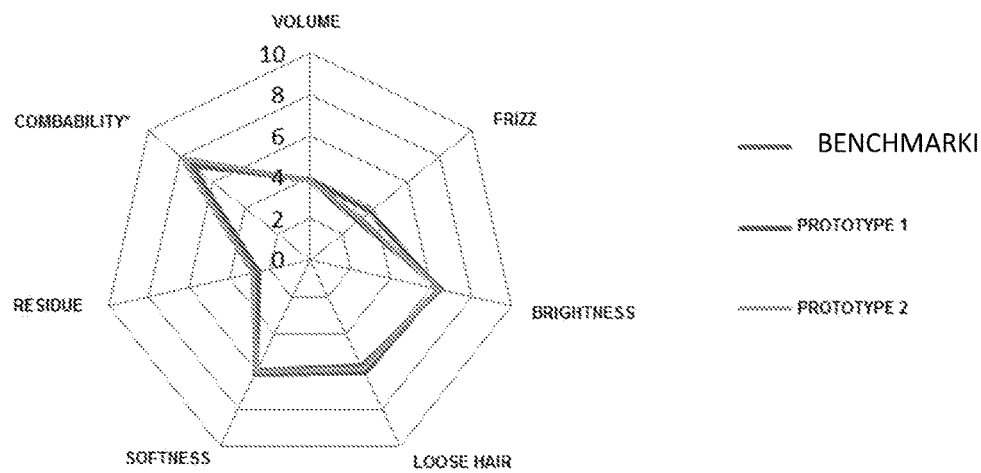
Fig. 5B – Evaluation of the dry hair

NANOSTRUCTURED CONDITIONING COSMETIC COMPOSITION, THE USE THEREOF IN COSMETIC PREPARATIONS, AND A CONDITIONING SHAMPOO

FIELD OF THE INVENTION

The present invention relates to conditioning cosmetic compositions comprising a nanostructured system formed by lipidic nanoparticles based on at least one from oil, butter and wax, which encapsulate at least one cationic surfactant, as well as the use thereof in the cosmetic, hygiene and personal-care industry. Besides, the invention relates to a conditioning shampoo comprising said cosmetic composition.

BACKGROUND OF THE INVENTION

The first compositions for shampoo were formulated exclusively for cleaning hair, not for conditioning them. With a view to innovate, providing convenience to the routine of caring for men's and women's hair, one introduced 2-in-1 shampoo, the technology of which has enabled one to introduce ingredients with conditioning properties into conventional shampoo compositions, by using ingredients that promote immediate conditioning by deposition onto the hair fiber, such as quaternized proteins, polyquaternium, silicones, among others. In conventional shampoos, the oily layer protecting the strands of hair is removed with anionic surfactants while cleaning the hair. In 2-in-1 shampoo, the anionic surfactants act cleaning the hair as a function of their detergent power, which captures dirty fragments and, sometimes, the above-cited conditioning ingredients and deposits them on the fiber and condition the strands.

Generally, the conditioning agents have positively charged molecules that neutralize the negative charges of the hair surface and aid in eliminating the repulsion of the strands, reducing frizz.

The great manufacturers of 2-in-1 shampoos usually employ to methods known in the prior art.

The first one, developed and marketed in the late Sixties and used until today, involves mixing cationic polymers with anionic shampoos.

The second method employed in 2-in-1 shampoos uses a micro suspension of silicone in anionic shampoo. The binding between the surfactant and the polymer is water-sensitive and, with the wash, the binding breaks and the surfactant separates from the conditioning polymer. Conditioning polymers, which are insoluble in water, remain on the hair, forming a layer that is deposited onto the strands and conditions them. Although these technologies are commercialized since decades ago, there are great challenges in using them, from both the technical point of view—as, for instance, the difficulty in preventing complexation between the conditioning agents and the surfactants—and the point of view of the consumer, since it is necessary to develop a composition with an appropriate balance of silicones and other conditioning ingredients that provide adequate conditioning, without leaving a residue that, with prolonged use, causes the undesirable effect known as build-up (the feeling of heavy hair due to accumulation of residues on the hair fiber).

With a view to optimize the 2-in-1-shampoo technology, the cosmetic industries have directed their researches to the promising area of nanotechnology. Nanotechnology is an innovative science that includes design, characterization, production and application of structures, devices and systems, controlling shape and size on the nanometric scale, on which 1 nanometer is 1 billionth of a meter. On the nanometric scale, the structures may acquire new properties. It is nothing new for the cosmetic companies that the nanotechnology is the way to the future and is considered the most emergent technology available.

With wide application in various types of cosmetic products, lipidic nanoparticles were considered excellent cosmetic release systems. Lipidic nanoparticles are basically a mixture of lipids and waxes in water, stabilized by surfactants and reduced to submicrometric sizes. These structures have various characteristics that are advantageous, as for example, high biocompatibility, chemical stabilization of actives, controlled release, among others.

The use of nanoparticles in the various industrial sectors evidences the importance of their physicochemical properties, proving to be a field that can grow even more, being highly promising, mainly in the area of cosmetics, which already had a market of 155.8 billion dollar in 2012.

A few examples of prior-art documents related to conditioning shampoos and possibly involving nanotechnology are presented hereinafter.

Patent EP 1465584, published on Jul. 10, 2003, in the name of Rhodia, relates to an aqueous cosmetic composition having a 2-in-1 shampoo. In order to solve the problem related to the combined use of anionic and cationic surfactants in 2-in-1 cosmetic compositions, the composition of said invention uses ammonium quaternaries, such as cetyltrimethyl ammonium chloride and behentrimonium chloride as cationic surfactants, alkyl sulfates as anionic surfactants, besides oily substances such as oils (almond oil and palm oil), waxes and derivatives of silicone, wherein the prior-art problem is solved with improvement of the stability of the composition at a low temperature. In spite of describing a cosmetic composition of the 2-in-1-shampoo type, said document does not deal with nanotechnology, or even the use of lipidic nanoparticles.

On the other hand, patent FR 2,920,983, published on Feb. 26, 2010, in the name of L'Oréal, relates to cosmetic compositions for use on hair in the form of oil-in-water (O/A) nanoemulsion with particle size smaller than 350 nm, comprising a cationic polymer and one or more cationic conditioning agents, which may be a cationic surfactant (cetyltrimethyl ammonium chloride and behentrimonium chloride), containing karité butter and palm oil. Patent EP 1,430,867, published on Feb. 10, 2010, also in the name of L'Oréal, relates to processes for preparing cosmetic compositions as well as to the cosmetic compositions themselves, for use on hair, in the form of nanoemulsion with particle size smaller than 100 nm, comprising cationic surfactants, karité butter, sweet-almond oil and palm oil as well.

Both documents above deal with nanoemulsions, called also mini-emulsions, sub-micron emulsions, ultrafine emulsions, among other names, which are transparent or translucent systems containing droplets on the nanoscale, usually with an average diameter ranging from 10 to 500 nm, depending on the preparation process. The main limitation for the development and application of nanoemulsions relates to the stability thereof. Although it is known that these systems could remain stable for years, Oswald ripening may cause instability in the system, making the use of nanoemulsions difficult. Thus, in many cases, it is necessary to prepare the nanoemulsions shortly before the use thereof. Besides, nanoemulsions generally exhibit lower capability of incorporating actives with respect to lipidic nanoparticles.

On the other hand, the present invention comprises lipidic nanoparticles consisting of a lipophilic solid matrix, in which active molecules may be incorporated. The particle size ranges mainly from 150 to 300 nm, wherein sizes smaller than <100 nm or bigger than 1000 nm may be obtained according to the preparation process and depending on the need and objectives. Lipidic nanoparticles may be derived from oil-in-water nanoemulsions, wherein the liquid lipid of the oil droplets is replaced by a solid lipid, that is, solid at body temperature. So, lipidic nanoparticles remain solid after administration to the body. Lipidic nanoparticles act as a matrix, protecting labile/instable and/or incompatible actives. They exhibit excellent physicochemical stability and greater capability to incorporate actives into the matrix, which may function as a controlled-release system.

Further with regard to the prior art, conditioning shampoos existing on the market, which use cationic polymeric conditioning agents, such as quaternized proteins, gums, polyquaternium, silicones, among others, have a few drawbacks. One of them is the technical challenge, since there may be complexation between the cationic agent and the anionic surfactant system, causing destabilization of the formulation.

Besides, compositions containing gums, silicones, quaternized proteins, etc, used in conditioning shampoos found on the market promote an immediate conditioning through mechanism of depositing material onto the hair fiber, by virtue of the molecular weight of these ingredients, but they do not treat the fiber internally. In the long run, they may further cause the undesirable build-up effect due to accumulation of product residues on one's hair.

Thus, one of the main objectives of the present invention is to bring about immediate and long-term conditioning through encapsulation of cationic surfactants, for instance, derived from quaternary ammonium, in lipidic nanoparticles using oils, butters and waxes, for instance, carnauba wax, as structuring agents of the lipidic carrier (lipidic nanoparticles), associating a long-term treatment effect through substantivity and regeneration of the hair fiber, as well as short-term cleansing effect, conditioning, improvement of combability, softness, brightness, decrease in frizz, decrease in volume, looser hair, among others. Since the positive charge of the conditioning system is not in contact with the negative charge of the shampoo base or other preparations for keratinic substrates (such as shampoos, toilet-soaps, conditioners, hydrating masks, leave-on, among other examples), by virtue of the nanoencapsulation process, the technical difficulty of handling the formulations is minimized, and thus the stabilization thereof is guaranteed. Besides, due to the nanometric size, the nanoparticles are expected to have a greater potential of penetration into the substrate (example: hair fiber), treating it internally instead of depositing only onto the outer area, which minimizes the build-up effect already mentioned before.

SUMMARY OF THE INVENTION

The present invention relates to conditioning cosmetic compositions comprising a nanostrucuted system formed by lipidic nanoparticles based on at least one from oil, butter and wax, which encapsulate at least one cationic surfactant.

The present invention further relates to a conditioning shampoo comprising the conditioning cosmetic composition of the present invention, as well as to the use of said conditioning cosmetic composition in various formulations, such as shampoos, 2-in-1 shampoos, conditioning shampoos, conditioners, hydrating masks, leave-on compositions, liquid and bar toilet-soaps.

BRIEF DESCRIPTION OF THE DRAWING FIGURES

Figure 1:
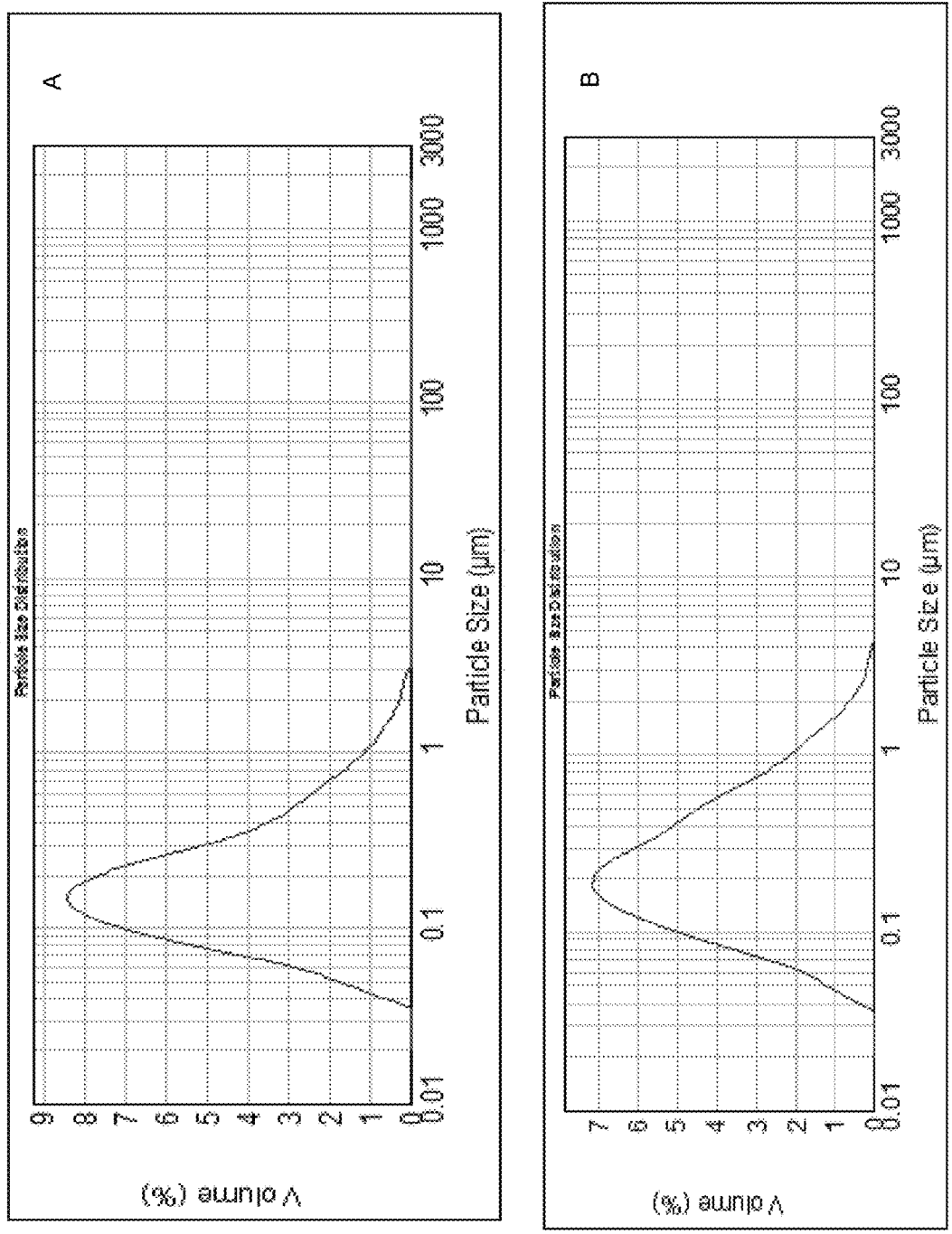
FIG. 1 is a graphic representation of the distribution of particle size after preparation of the lipidic particles (A) and a distribution of the particle size after storage at 45° C. for 90 days.

FIGS. 5A and 5B reflect an evaluation of the products of the claimed invention using wet hair (FIG. 5A) and dry hair (FIG. 5B).

DETAILED DESCRIPTION OF THE INVENTION

The conditioning cosmetic compositions of the present invention comprise a nanostructured system formed by lipidic nanoparticles, which are basically a mixture of lipids and waxes in water, stabilized by surfactants/emulsifiers, and reduced to submicrometric sizes by the high-pressure homogenization process.

When said lipidic nanoparticles are measured by laser diffraction (MasterSizer MicroPlus), their size ranges from 50 to 1000 nm, particularly from 60 to 800 nm, more particularly from 90 to 700 nm. The average size of said particles ranges from 230±nm (D 0.5).

When these lipidic nanoparticles are measured by photon correlation spectrocospy (Delsa™ Nano), their size ranges from 50 to 500 nm, particularly from 60 to 400 nm, more particularly from 85 to 350 nm. The average size of said particles ranges from 167±4 nm (D 0.5).

Nanoparticles have advantageous characteristic for the preparation of the conditioning shampoo, since they encapsulate cationic surfactants and are composed by ingredients of lipidic nature, such as oils, waxes, butters, and emulsifiers, preferably silicones, which together with cationic surfactants promote hair conditioning. Nanoparticles also help in stabilizing the conditioning shampoo, since they prevent the positive charge of the cationic surfactant from interacting with the negative charge of the anionic surfactant system of the shampoo.

According to a preferred embodiment of the present invention, the conditioning cosmetic composition of the present invention comprises:

at least one from cetyltrimethyl ammonium chloride and behentrimonium chloride, in an amount ranging from 0.1 to 99% by weight, preferably from 1 to 60%, more preferably from 5 to 40%, as cationic surfactants;

at least one from lauryl glycoside, decyl glycoside, sorbitan stearate in an amount ranging from 0.01 to 50% by weight, preferably from 0.1 to 20%, more preferably from 0.2 to 5%, as non-ionic surfactants;

at least one cyclopentasiloxane, copolyol dimethicone, cyclomethicone D5, dimethiconol, dimethicone 20/350 in an amount ranging from 0.01 to 40% by weight, preferably from 0.1 to 20%, more preferably from 0.5 to 10%, as compounds derived from silicone having emollient and film-forming function;

at least one from waxes, oils, butters in an amount ranging from 0.01 to 50% by weight, preferably from 0.1 to 20%, more preferably from 0.5 to 10%, having the emollient and lipidic-nanoparticle structuring agent function;

one or more active ingredients, as well as adjuvants usually employed in the cosmetic, hygiene and personal-care industry, and a cosmetically acceptable carrier.

Said active ingredients and adjuvants that are suitable for the purposes of the cosmetic compositions of the invention, correspond to those that are usually employed in the cosmetic, hygiene and personal-care industry, being selected, for instance, from the group consisting of plant oils such as sweet-almond and palm oil, butters such as karité butter and waxes such as carnauba wax or any other oils, butters and waxes with similar physico-chemical characteristics. Besides, demineralized water, antioxidants, pre-servers, chelants, among others, may be used as adjuvants.

The conditioning cosmetic composition of the invention may further be applied to shampoos, conditioners, hydrating masks, leave-on compositions, liquid toilet-soaps and bar toilet-soaps. The composition of the invention may be formulated in the form of a bar, solution, gel, cream, among others.

The shampoo-based composition with high conditioning power to which the conditioning cosmetic composition is added comprises:

lauryl ether sodium sulfate in an amount ranging from 0.1 to 100%, preferably from 1 to 70%, more preferably from 10 to 50%, as anionic surfactant;

guar hydroxypropyltrimonium chloride in an amount ranging from 0.001 to 30%, preferably from 0.01 to 5%, more preferably from 0.1 to 2%, as a conditioning and film-forming agent;

ocamidopropyl betaine in an amount ranging from 0.1 to 98%, preferably from 1 to 50%, more preferably from 5 to 20%, as amphoterous surfactant;

dimeticonole TEA-dodecylbenzenesulfonate in an amount ranging from 0.01 to 30%, preferably from 0.1 to 10%, more preferably from 0.5 to 5%, as a compound derived from silicone having the emollient and conditioning function;

particulate polymer of acrylate/alkyl acrylate C10-30 in an amount ranging from 0.01 to 20%, preferably from 0.1 to 10%, more preferably from 0.5 to 1.5%, as a suspending and cross-linking agent;

nanostructured conditioning cosmetic composition of the present invention in an amount ranging from 0.001 to 100% by weight, as a conditioning system, preferably from 0.01 to 20%, more preferably from 0.5 to 10% when used in shampoo formulations.

Additionally, adjuvants that are usually employed in the cosmetic, hygiene and personal care industry may be included in the conditioning shampoo composition of the invention, which may be preferably selected from the group consisting of antioxidants, film-forming agents, moistening agents (humectants and emollients), preservers, thickeners, pH adjusters, sequestering agents (or chelating agents), fragrances or perfumes, cleansing agents and other cosmetically acceptable components. A person skilled in the art will know how to select the ingredients and the adequate amounts thereof.

The conditioning cosmetic composition of the present invention has a number of advantages and characteristics desired in a cosmetic product, particularly one for hair, these advantages being achieved with the optimum combination between the already-described components, some of which are listed below:

a differentiated conditioning effect;

substantivity;

softness;

excellent combability;

reduction of frizz;

brightness; and lightness.

The embodiments of the invention exemplified hereinafter are intended for illustrating, without limiting the scope of the object in any way.

EXAMPLES

Example 1—A Conditioning Cosmetic Composition

Table 1 below presents the formulation of a conditioning cosmetic composition according to the present invention.

TABLE 1

| Component | Concentration (% by weight) |
|---|---|
| Organic carnauba wax | 2% |
| Sweet almond oil | 4% |
| Karité butter | 1% |
| Dimeticone 200/350 | 4% |
| Sorbitan stearate | 0.5% |
| Cyclomethicone D5 and dimethiconol | 1% |
| BHT | 0.05% |
| Refined palm oil | 6% |
| Cyclopentasiloxane and copolyol dimethicone | 2% |
| Methylchloroisothiazolinone and methylsothiazolinone | 0.05% |
| Lauryl glycoside | 1.5% |
| Decyl glycoside | 1% |
| Cethyltrimethylamonium chloride | 40% |
| Behentrimonium chloride | 5% |
| Demineralized water | 31.9% |

Said conditioning cosmetic composition of the present invention was prepared as follows:

1) heating the water up to 60° C.;

2) adding behentrimonium chloride under stirring; keeping the stirring and heating until solubilization of the behentrimonium; also adding the cetyltrimethylamonium chloride under stirring;

3) at 75° C. initiate the addition of the other components (oils, butter and surfactants—with the exception of carnauba wax and methylchloroisothiazolinone). After addition of carnauba wax (at 80° C.), heat until 85° C. under stirring;

4) after preparation of this pre-emulsion, subjecting it to homogenization under high pressure (at least for 2 cycles at 600 bar and 1200 bar). After cooling, adding methylcloroisothiazolinone and methylisothiazolinone.

Example 2—Shampoo

Table 2 below presents an example of formulation of the shampoo composition with high conditioning power (prototype 1), to which the conditioning cosmetic composition of example 1 is added.

TABLE 2

| Component | Concentration (% by weight) |
| --- | --- |
| Demineralized water | 45.77% |
| Carbopol ETD 2020 | 0.9% |
| Tetrasodic EDTA | 0.1% |
| Trietanolamine | 1.4% |
| Guar hydroxypropyltrimonium chloride | 0.2% |
| Cocamidopropoyl betaine | 9% |
| Lauryl ether sodium sulfate | 37.1% |
| Dimethiconol TEA dodecylbenzenesulfonate | 1% |
| Methylchloroisothiazolinone and methylisothiazolinone | 0.03% |
| Fragrance | 0.5% |
| Formulation of Example 1 | 4% |

Said cosmetic composition is prepared in a conventional way and is known to those skilled in the art.

Example 3—Shampoo

Table 3 below presents another example of formulation of the shampoo-base composition with high conditioning power (prototype 2), to which the conditioning cosmetic composition of example 1 is added.

TABLE 3

| Component | Concentration (% by weight) |
| --- | --- |
| Demineralized water | 46.77% |
| Carbopol ETD 2020 | 1.10% |
| Tetrasodic EDTA | 0.1% |
| Triethanolamine | 1.4% |
| Cocamidopropyl betaine | 9% |
| Lauryl ether sodium sulfate | 37.1% |
| Methylchloroisothiazolinone and methylisothiazolinone | 0.03% |
| Fragrance | 0.5% |
| Formulation of Example 1 | 4% |

Example 4—Process of Preparing the Conditioning Shampoo of the Invention

The conditioning cosmetic composition of example 1 of the invention is prepared as described in Example 1 above.

The shampoo-base compositions with high conditioning power of examples 2 and 3 of the invention are prepared as follows:
a) carbopol is dissolved in water and EDTA is neutralized with triethanolamine until the pH range of 6.0-7.0 is reached;
b) in parallel, guar hydroxypropyltrimonium chloride (when present in the formulation) is dissolved in 6% water;
c) adding dissolved guar hydroxypiltrimonium chloride to the neutralized carbopol;
d) after adding Cocamidopropyl betaine, homogenize sufficiently and then adding lauryl ether sodium sulfate and homogenize;
e) in the absence of lumps, continue adding the other ingredients of the formulation, under constant stirring. The Formulation of Example 1 should be added last and under stirring to obtain the conditioning shampoo of the invention.

Tests
Test 1—Studies of Characterization of the Nanoparticles
1.1—Analysis of Particle Size and Distribution The analyses of particle size were carried out by using two different techniques: laser diffraction (MasterSizer MicroPlus) and photon correlation spectroscopy (Delsa™ nano).

The average particle sizes were of 230±7 nm (Master-Sizer-3 different batches) and 167±4 nm (Delsa™ Nano).

The different batches were stored in different conditions (dark, sun light, 5° C., 37° C. and 45° C.) for 90 days. FIG. 1 shows the distribution of particle size after storage at 45° C. for 90 days.

The results showed that nanoparticles are stable, even in conditions of varying temperature and that no significant changes in the analyses of particle size were observed.

1.2—Dynamic Turbidimetry of Vertical Scanning (TURBISCAN®)

The analytic technique of dynamic turbidimetry of vertical scanning was employed for characterization of the samples by using an equipment of Turbiscan Lab model, manufactured by Formulation Inc. The software Turbisoft Version 1.13 EXPERT was used for managing the experiments and treating the results achieved. The analyses were carried out individually in a continuous manner during a total time interval of 24 hours, wherein the intermediate obtainment of results was made every 1-hour interval. The registering of the experimental data considered simultaneously the amount of backspread (BS) light and the amount of transmitted light (T). The tests were conducted in conditions of room temperature, using a thermostatization system that enabled the operation in values of 25±1° C.

The operation principle of the vertical scanning dynamic turbidimeter is based on the interaction of a beam of light from an electroluminescent diode in the near infrared range (880 nm) with the sample packed in a glass cell. Two synchronous optical sensors receive, respectively, the fraction of light transmitted through (transmission detector—position 180 degree with respect to the incident beam) and the fraction of light backspread by the sample (backspreading detector—position 45 degrees with respect to the incident radiation). The operation of the equipment is such that in vertical scanning its optical reading head moves along the height of the sample, and the transmittance and backspreading data will be registered every 40 μm-interval. The operation mode in question enables a complete and comprehensive analysis with regard to the stability evaluation topic, since it provides detection and the respective determination of kinetic parameters related to different phenomena of phase separation.

Figure 2:
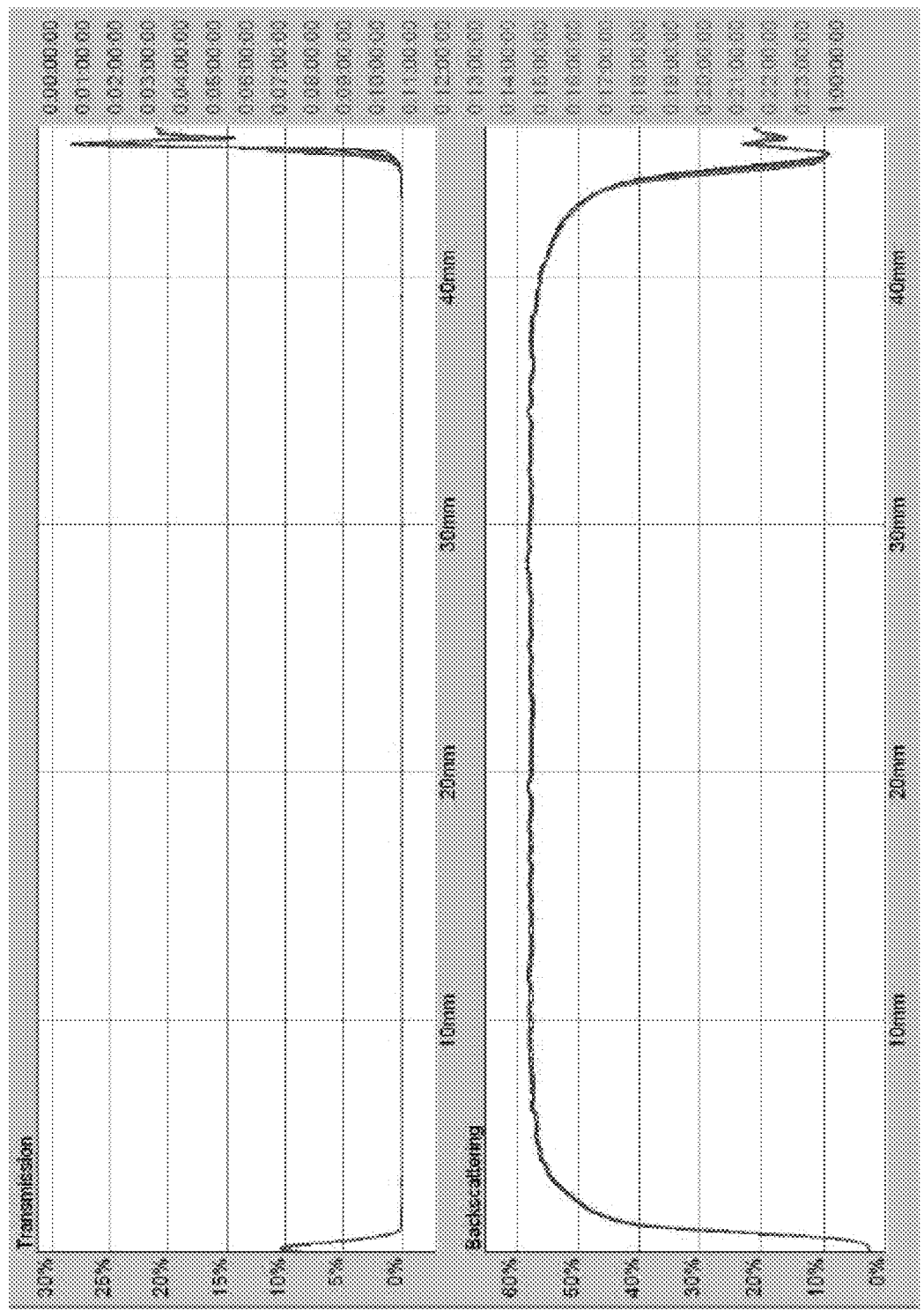
FIG. 2 is a graphic representation demonstrating the dynamic turbidity of vertical scanning (TURBISCAN®) analysis.

The attached FIG. 2 demonstrates that the light was not transmitted during the analysis, identifying the system as being opaque. In this case, only backspread light is used in interpreting the results. The BS graph shows the extremely low variation in reading in 24 hours' analysis, which demonstrates the physical stability of the system, and no coalescence, flocculation, sedimentation and creaming phenomena were observed.

1.3—Determination of the Zeta Potential

The conventional light-spreading technique that measures the variation of the frequency of a laser beam (Doppler effect) was employed for experimental determination of the values of electrophoretic mobility, defined as being the ratio between the resulting velocity and the magnitude of the electric field applied. The equipment employed was an electrophoretic analyzer model Malvern ZetaMaster S. The ratio proposed by Smoluchowsky was applied for conversion of the values of electrophoretic mobility in zeta potential.

The preparation of the samples was restricted to the process of dilution of the material in an aqueous medium at a ratio of 1:500 by volume, so as to ensure a level of photocount intensity required for reliability of the results obtained. The tests were carried out in triplicate, contemplating ten consecutive measurements for each sample. The results presented in Table 4 correspond to the average of the experimental registers obtained for each of the analyzed samples.

TABLE 4

Measurements of Zeta potential

| Assay | Lipidic nanoparticles | Shampoo containing lipidic nanoparticles |
|---|---|---|
| 1 | 52.70 ± 1.5 mV | −44.28 ± 0.25 mV |
| 2 | 48.49 ± 1.08 mV | −47.51 ± 4.02 mV |
| 3 | 51.18 ± 8.47 mV | −47.76 ± 5.76 mV |

Thee readings were carried out on the sample of the lipidic carrier-lipidic nanoparticles and of the shampoo containing this carrier. The positive values for the lipidic carrier indicate a high zeta potential with cationic charge, due to its chemical composition and the objective of this project. This zeta potential confirms the production of cationic lipidic carriers. The shampoo with the cationic carriers (lipidic nanoparticles) incorporated kept their anionic nature, typical of the presence of surfactants of the type lauryl ether sodium sulfate. The lower influence of the carrier on the zeta potential of the shampoo is an indication of the maintenance of its stability and of the non-reduction of the cleansing capability of the final product.

1.4—Morphological Analysis Through Electronic Transmission Microscopy

The samples of lipidic nanoparticles were diluted at 10% in purified water. The diluted samples were applied in copper grids for 1 minute and contrasted with uranyl acetate 2% on the same grids for 1 minute. After this time, the samples were dried with filter paper, allowed to stand for 24 hours before the analyses. The photomicrographs were carried out on JEOL JEM 1200 ExII Electronic Transmission Microscope at different enlargements.

Figure 3:
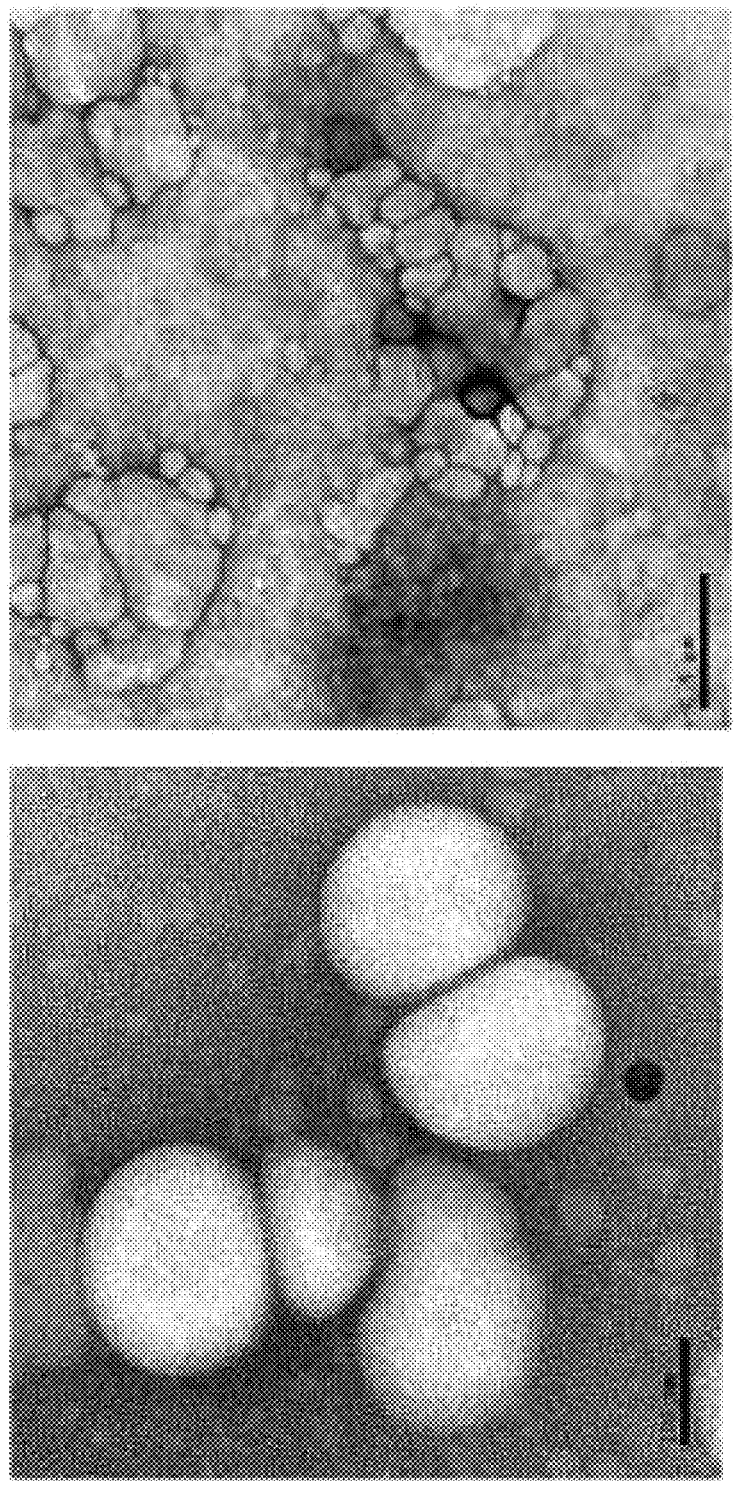
FIG. 3 illustrates photomicrographs obtained by electronic transmission microscopy of the lipidic particles.

The microscopy images exhibit spheroid spherical particles, with a diameter similar to that analyzed by laser diffraction and photon correlation spectroscopy. One can see that, even drying the sample, there was no coalescence between particles, which remained whole and well defined. There is no evidence of mixture of types of nanostructures in the samples, but rather of a single population of particles. FIG. 3 illustrates one of the photomicrographs obtained by electronic transmission microscopy.

From the characterization made above, we can conclude that the nanostructured lipidic carriers (lipidic nanoparticles) have a diameter suitable for application in keratin substrates, ranging from 160 to 230 nm on average, with a low polydispersion rate. They are stable along the time and after incorporation into the shampoo base. They have a positive surface charge, with cationic surfactants adsorbed on the surface, suitable for promoting conditioning, which, however, do not interfere with the charge and the stability of the surfactant preparations.

Test 2—Safety Tests
2.1—Genotoxicity Test

The micronucleus test is a test that enables one to detect the chromosome break. This type of injury is classified as a global damage which may occur to the DNA, that is, genotoxicity. In this study, the objective is to evaluate the direct genotoxicity potential of the conditioning cosmetic composition (lipidic nanoparticles), with formulation according to example 1, using the in vitro micronucleus test (MN-vit).

Micronucleus are small fragments of DNA that do not migrate correctly during the anaphase. They result from different damages to the DNA like chromosome breaks (clastogenic activity) or non-migration of chromosomes (aneugenic activity). In this test, the CHO-K1 cells are cultivated and exposed to a range of dosage of the chemical product to be tested. First, the maximum dose to be tested is determined by a cytotoxicity study using the NRU test. The maximum dose retained has to enable at least 80±10% feasibility. For this test of micronuclei, after the treatment, the cell is cultivated so that it can start mitosis. The mitosis is then interrupted, and the cells that initiated the division are now with two nuclei (binucleated cells). These binucleated cells are evaluated in order to verify whether they contain any micronucleus. The final rate of binucleated cells with micronuclei is compared with the control cell culture that was treated with the carrier alone. A statistic increase in the rate of micronucleated cells indicates that the chemical product tested exhibits genotocic activity.

In this test, the conditioning cosmetic composition (lipidic nanoparticles) tested at concentrations of 0.001%, 0.0005% and 0.0001% were classified as "undetected direct genotoxicity".

2.2—Mutagenicity Test

The Ames test, a mutagenic assay on prokaryotic cells of *Salmonella typhimurium*, derived from the parental stem LT2 auxotrophic for histidine, was conducted for the conditioning cosmetic composition, with formulation according to example 1. In addition to the mutation for histidine, such standard strains have other mutations that increase gradually their capability to detect mutagenics. These strains are incapable of growing in a culture medium without histidine, unless mutations will establish reversions that restore the synthesis of histidine. The reversion frequency is measured by the count of colony forming units of cell population that has been exposed to a mutagenic substance. The number of revertants per dose of the substance under test is calculated for each strain, and the results are also analyzed by statistic methods.

In this test, the conditioning cosmetic composition of the present invention did not induce to mutagenic activity in *Salmonella typhimurium* strains used in the assay.

Other safety studies like cytotoxicidy, phototoxicity, equivalent skin (EpiSkin®) and patch test were also carried out, and the results showed that the nanoparticles are not toxic and exhibit biocompatibility.

Test 3—Efficacy Test
3.1—Substantivity Test

Measurements on substantivity of chemical components present in cosmetic formulations may be carried out by various methodologies, but none of them is as accurate as the use of the technique of marking components by fluorescent molecules by using fluorescence microscopy. The use of this technique enables one to discriminate the components present both on the surface of the hair fiber and inside it. Experimentally, there is a great difficulty in detecting the microscopic distribution of small amounts of substances within another similar chemical composition, as for example, amino acids. An essential requirement is the process of treating and selecting the fluorescent component; the advantage of using this specific technique is the high specificity of selection through fluorescent emission of the marker.

In this study, one used the dye Rodamina B (CI Basic Violet 10), a cationic dye that reacts with the active sites of the sulfonic acid, formed by cleaving the S—S bond of cystine (disulfidic bonds) caused in the hair relaxation process. Then a fluorescent complex is formed on the hair fiber, which is detected when the latter is exposed to the fluorescence microscope coupled to the filters compatible with the wavelength emitted.

Figure 4:
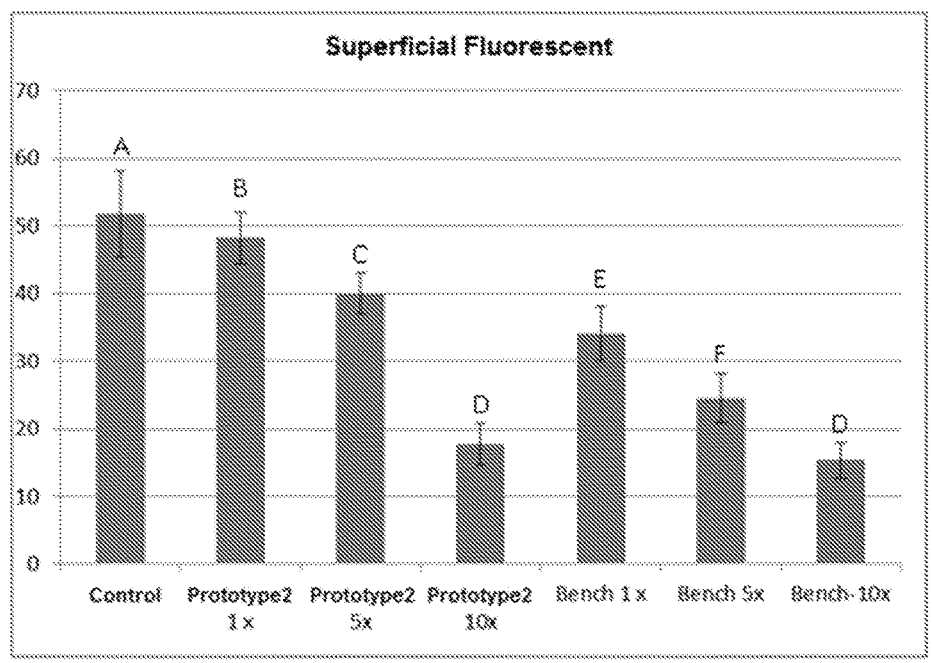
FIG. 4 is a graphic representation of the hair substantivity study reflecting the statistic differences between a control and the shampoo containing lipidic nanoparticles.

The lower the fluorescence intensity the better the performance of the product in filling and nourishing the hair fiber. The results show that the shampoo containing lipidic nanoparticles (prototype 2-example 3) exhibit greater substantivity as compared with the control (shampoo containing lauryl ether sodium sulfate without nanoparticles) and the performance is equivalent to the benchmarking after 10 applications (FIG. 4).

3.2—Trained Panel

A trained panel was carried out with professional hair stylists, using the methodology of descriptive analysis by free profile. Each prototype was applied in half head according to a standardized and validated evaluation protocol. Different attributes were validated while washing the hair, on wet hair and on dry hair (results presented in Tables 5 and 6 below and FIGS. 5A and 5B).

TABLE 5

Evaluation while washing and on wet hair

|  | BENCH | PROTOTYPE 1 | PROTOTYPE 2 |
| --- | --- | --- | --- |
| CONSISTENCY* | 5.96 | 4.96 | 4.00 |
| SPREADABILITY - APPLICATION* | 4.89 | 5.80 | 6.15 |
| AMOUNT FOAM* | 6.64 | 5.04 | 5.44 |
| CREAMINESS FOAM* | 6.325 | 6.88 | 6.78 |
| PREVIOUS DISENTANGLEMENT WITH FINGERS | 5.17 | 5.84 | 6.05 |
| RINSING | 5.95 | 5.86 | 5.56 |
| DISENTANGLEMENT WITH FINGERS | 5.40 | 5.76 | 6.24 |
| CLEANLINESS* | 6.41 | 6.47 | 5.90 |
| DISENTANGLEMENT WITH A COMB | 5.53 | 5.81 | 6.33 |
| SOFTNESS - WET | 5.71 | 5.72 | 6.29 |

*Attribute with statistic difference at $p \leq 0.05$

TABLE 6

Evaluations on dry hair

|  | BENCH | PROTOTYPE 1 | PROTOTYPE 2 |
| --- | --- | --- | --- |
| VOLUME | 3.83 | 3.90 | 3.81 |
| FRIZZ | 2.97 | 3.71 | 3.15 |
| BRIGHTNESS | 6.50 | 6.37 | 6.37 |
| LOOSE HAIR | 5.67 | 6.09 | 5.87 |
| SOFTNESS | 5.96 | 6.13 | 6.01 |
| RESIDUE | 2.51 | 2.61 | 2.85 |
| COMBABILITY | 7.37 | 7.28 | 7.92 |

* Attribute with statistic difference at $p \leq 0.05$

After statistic analysis of the results (ANOVA and Tukey), one can conclude that the prototypes containing lipidic nanoparticles showed performance equivalent to the benchmarking in different attributes such as: feeling of cleanliness, softness, frizz, volume, brightness, ease of combing, among others. Considering the attributes of foam creaminess and stability, the prototypes 1 and 2 exhibited performance superior to the bench and in combability after drying the hair, the prototype 2 being superior to the others.

The invention claimed is:

1. A conditioning cosmetic composition comprising a nanostructured system formed by solid lipidic nanoparticles based on at least one from oil, butter and wax, and at least one cationic surfactant encapsulated in said solid lipidic nanoparticles.

2. The conditioning cosmetic composition according to claim 1, wherein the cationic surfactant is selected from the group consisting of cetyltrimethyl amonium chloride and behentrimonium chloride.

3. The conditioning cosmetic composition according to claim 2, wherein the cationic surfactant is present in an amount ranging from 0.1 to 99% by weight, preferably from 1 to 60%, more preferably from 5 to 40%, based on the total weight of the composition.

4. The conditioning cosmetic composition according to claim 1, wherein said at least one from oil, butter and wax is present in an amount ranging from 0.01 to 50% by weight, preferably from 0.1 to 20%, more preferably from 0.5 to 10%, based on the total weight of the composition.

5. The conditioning cosmetic composition according to claim 1, wherein the oil is plant oil selected from the group consisting of sweet-almond oil and palm oil.

6. The conditioning cosmetic composition according to claim 1, wherein the butter is Karité butter.

7. The conditioning cosmetic composition according to claim 1, wherein the wax is carnauba wax.

8. The conditioning cosmetic composition according to claim 1, further comprising at least one from emollient and film-forming agent.

9. The conditioning cosmetic composition according to claim 8, wherein said at least one from emollient and film-forming agent is selected from the group consisting of cyclopentasiloxane, copolyol dimethicone, cyclomethicone D5, dimethiconol and dimethicone 200/300.

10. The conditioning cosmetic composition according to claim 8, wherein said at least one from emollient and film-forming agent is present in an amount ranging from 0.01 to 40% by weight, preferably from 0.1 to 20%, more preferably from 0.5 to 10%, based on the total weight of the composition.

11. The conditioning cosmetic composition according to claim 1, wherein the nanoparticles have size in the range 50 to 1000 nm, when measured by laser diffraction (Master-Sizer MicroPlus).

12. The conditioning cosmetic composition according to claim 1, further comprising cosmetic adjuvant selected from the group consisting of antioxidants, preservatives, thickener, pH adjusters, sequestering agents (quelants), fragrances or perfumes, cleansing agents and other cosmetically acceptable components.

13. The conditioning cosmetic composition according to claim 1, further comprising a non-ionic surfactant.

14. The conditioning cosmetic composition according to claim 13, wherein the non-ionic surfactant is selected from the group consisting of lauryl glycoside, decyl glycoside and sorbitan stearate.

15. The conditioning cosmetic composition according to claim 13, wherein the non-ionic surfactant is present in an amount ranging from 0.01 to 50% by weight, preferably from 0.1 to 20%, more preferably from 0.2 to 5%, based on the total weight of the composition.

16. The conditioning cosmetic composition according to claim 1, wherein it can be used in shampoo formulations, 2-in-1 shampoos, conditioning shampoos, conditioners, hydrating masks, leave-on compositions, liquid toilet soaps or bar toilet soaps.

17. A conditioning shampoo comprising the conditioning cosmetic composition according to claim 1.

18. The conditioning shampoo according to claim 17, wherein the cosmetic composition is present in an amount ranging from 0.001 to 100% by weight, based on the total weight of the composition.

19. The conditioning cosmetic composition according to claim 1, wherein said composition is adapted for use in shampoo formulations, 2-in-1 shampoos, conditioning shampoos, conditioners, hydrating masks, leave-on compositions, liquid toilet soaps or bar toilet soaps.

20. The conditioning shampoo according to claim 17, wherein the cosmetic composition is present in an amount ranging from 0.01 to 20%.

21. The conditioning shampoo according to claim 17, wherein the cosmetic composition is present in an amount ranging from 0.5 to 10%.

* * * * *